(12) United States Patent
Kuo

(10) Patent No.: US 12,329,646 B2
(45) Date of Patent: Jun. 17, 2025

(54) FEMORAL HEAD ARTHROPLASTY SYSTEM

(71) Applicant: United States Government as Represented by the Department of Veterans Affairs, Washington, DC (US)

(72) Inventor: Alfred Kuo, San Francisco, CA (US)

(73) Assignee: United States Government As Represented By The Department Of Veterans Affairs, Washington, DC (US)

( * ) Notice: Subject to any disclaimer, the term of this patent is extended or adjusted under 35 U.S.C. 154(b) by 17 days.

(21) Appl. No.: 17/536,798

(22) Filed: Nov. 29, 2021

(65) Prior Publication Data

US 2022/0079767 A1     Mar. 17, 2022

Related U.S. Application Data

(62) Division of application No. 16/899,230, filed on Jun. 11, 2020.
(Continued)

(51) Int. Cl.
*A61F 2/36*     (2006.01)
*A61B 17/74*     (2006.01)
(Continued)

(52) U.S. Cl.
CPC .. *A61F 2/3609* (2013.01); *A61F 2002/30433* (2013.01); *A61F 2002/30784* (2013.01);
(Continued)

(58) Field of Classification Search
None
See application file for complete search history.

(56) References Cited

U.S. PATENT DOCUMENTS 2,668,531 A * 2/1954 Haboush ................ A61F 2/32
623/23.13
3,781,917 A * 1/1974 Mathys .................. A61F 2/36
606/65
(Continued)

FOREIGN PATENT DOCUMENTS

DE     2832555 A1 * 7/1978
DE     8518396 U1 * 6/1985
(Continued)

OTHER PUBLICATIONS

International Search Authority Search Report and Written Opinion for 37759.0172P1, dated Aug. 28, 2020.

*Primary Examiner* — Ann Hu
(74) *Attorney, Agent, or Firm* — Ballard Spahr LLP

(57) ABSTRACT

A femoral head arthroplasty system can comprise a femoral prosthesis comprising a mounting plate having a first side and an opposed second side. An adapter can extend from the second side of the mounting plate. An implant body can extend from the first side of the mounting plate. The implant body can extend from the mounting plate by a distance no greater than 90 mm. The femoral head arthroplasty system can further comprise a femoral head replacement having a generally spherical surface and comprising a recess that is shaped to complementarily receive the adapter of the femoral prosthesis.

10 Claims, 18 Drawing Sheets

Related U.S. Application Data

(60) Provisional application No. 62/860,549, filed on Jun. 12, 2019.

(51) Int. Cl.
*A61B 17/86* (2006.01)
*A61F 2/30* (2006.01)
*A61F 2/40* (2006.01)

(52) U.S. Cl.
CPC ........... *A61F 2002/3093* (2013.01); *A61F 2002/3611* (2013.01); *A61F 2002/365* (2013.01); *A61F 2310/00023* (2013.01); *A61F 2310/00029* (2013.01); *A61F 2310/00131* (2013.01); *A61F 2310/00574* (2013.01); *A61F 2310/00616* (2013.01); *A61F 2310/00634* (2013.01); *A61F 2310/00796* (2013.01); *A61F 2310/0088* (2013.01)

(56) References Cited

U.S. PATENT DOCUMENTS

| | | | | |
|---|---|---|---|---|
| 3,987,499 | A * | 10/1976 | Scharbach | A61F 2/30767 606/247 |
| 4,129,903 | A * | 12/1978 | Huggler | A61F 2/3601 623/23.11 |
| 4,532,660 | A * | 8/1985 | Field | A61F 2/3601 623/23.42 |
| 4,770,660 | A * | 9/1988 | Averill | A61F 2/4637 623/23.22 |
| 4,770,661 | A * | 9/1988 | Oh | A61F 2/32 623/22.2 |
| 5,030,238 | A * | 7/1991 | Nieder | A61F 2/30749 623/22.42 |
| 5,112,333 | A | 5/1992 | Fixel | |
| 5,167,666 | A * | 12/1992 | Mattheck | A61F 2/36 606/62 |
| 5,376,126 | A * | 12/1994 | Lin | A61F 2/3601 623/23.11 |
| 5,458,654 | A * | 10/1995 | Tepic | A61B 17/1753 606/62 |
| 5,571,202 | A * | 11/1996 | Mathys, Sr. | A61F 2/3662 623/23.27 |
| 5,571,203 | A * | 11/1996 | Masini | A61F 2/3601 623/22.46 |
| 5,645,607 | A * | 7/1997 | Hickey | A61F 2/4684 623/23.35 |
| 6,383,227 | B1 * | 5/2002 | Baroud | A61F 2/3601 623/23.22 |
| 6,409,768 | B1 | 6/2002 | Tepic | |
| 6,706,073 | B2 * | 3/2004 | Draenert | A61F 2/36 623/23.26 |
| 6,783,549 | B1 * | 8/2004 | Stone | A61B 17/1684 623/18.11 |
| 7,374,576 | B1 * | 5/2008 | Ries | A61F 2/36 623/23.35 |
| 7,569,075 | B2 * | 8/2009 | Johnson | A61F 2/3601 623/22.44 |
| 7,695,502 | B2 | 4/2010 | Orbay | |
| 8,252,062 | B2 * | 8/2012 | Bandoh | A61F 2/3662 623/23.18 |
| 8,398,719 | B2 * | 3/2013 | Walter | A61F 2/3601 623/23.35 |
| 8,470,049 | B2 * | 6/2013 | Walter | A61F 2/3662 623/23.35 |
| 8,840,675 | B2 | 9/2014 | Song | |
| 8,968,415 | B2 * | 3/2015 | Meridew | A61F 2/3601 623/22.4 |
| 9,295,556 | B2 | 3/2016 | Perez, III | |
| 9,402,728 | B2 | 8/2016 | Liu | |
| 9,427,321 | B2 | 8/2016 | Termanini | |
| 9,782,208 | B2 | 10/2017 | Martin | |
| 9,974,656 | B2 * | 5/2018 | Pappas | A61F 2/3601 |
| 10,034,758 | B2 * | 7/2018 | Winslow | A61F 2/4014 |
| 10,166,032 | B2 * | 1/2019 | Stone | A61F 2/4003 |
| 2002/0111689 | A1 | 8/2002 | Hyde, Jr. | |
| 2002/0120343 | A1 | 8/2002 | Doubler | |
| 2002/0133234 | A1 * | 9/2002 | Sotereanos | A61B 17/1753 623/23.26 |
| 2006/0015188 | A1 * | 1/2006 | Grimes | A61F 2/3601 623/23.22 |
| 2007/0055248 | A1 | 3/2007 | Zlowodzki | |
| 2007/0255420 | A1 | 11/2007 | Johnson et al. | |
| 2008/0004711 | A1 * | 1/2008 | Li | A61F 2/3601 623/23.22 |
| 2009/0118773 | A1 | 5/2009 | James | |
| 2009/0192550 | A1 | 7/2009 | Zafer | |
| 2009/0210067 | A1 | 8/2009 | Meridew | |
| 2011/0196491 | A1 * | 8/2011 | Huebner | A61B 17/1778 623/16.11 |
| 2012/0010722 | A1 * | 1/2012 | Walter | A61F 2/3609 623/23.18 |
| 2012/0259422 | A1 | 10/2012 | Pappas et al. | |
| 2013/0144397 | A1 | 6/2013 | Smith et al. | |
| 2013/0158608 | A1 | 6/2013 | Viola | |
| 2014/0066998 | A1 | 3/2014 | Martin | |
| 2014/0094926 | A1 | 4/2014 | Huff | |
| 2014/0180289 | A1 | 6/2014 | Lee | |
| 2014/0257512 | A1 | 9/2014 | Liu | |
| 2016/0331426 | A1 | 11/2016 | Tao | |
| 2017/0095279 | A1 | 4/2017 | Bare | |

FOREIGN PATENT DOCUMENTS

| | | | |
|---|---|---|---|
| DE | 19725269 C2 * | 11/1999 | ........... A61F 2/3601 |
| EP | 0099167 A1 * | 5/1982 | |
| EP | 1205163 A1 * | 5/2002 | ............ A61B 17/15 |
| FR | 2438470 A1 * | 10/1978 | |
| FR | 2674122 A1 * | 9/1992 | ........ A61B 17/1721 |
| WO | WO-8911837 A * | 12/1989 | .............. A61F 2/32 |
| WO | WO-2006004401 A2 * | 1/2006 | ........... A61F 2/3601 |
| WO | WO2010118894 A2 | 10/2010 | |

* cited by examiner

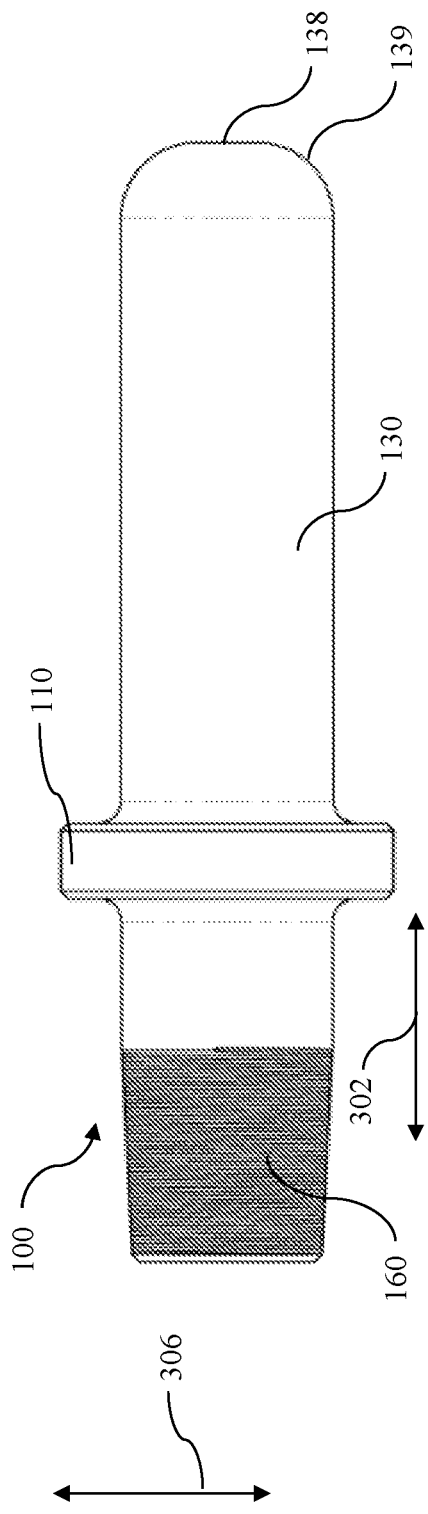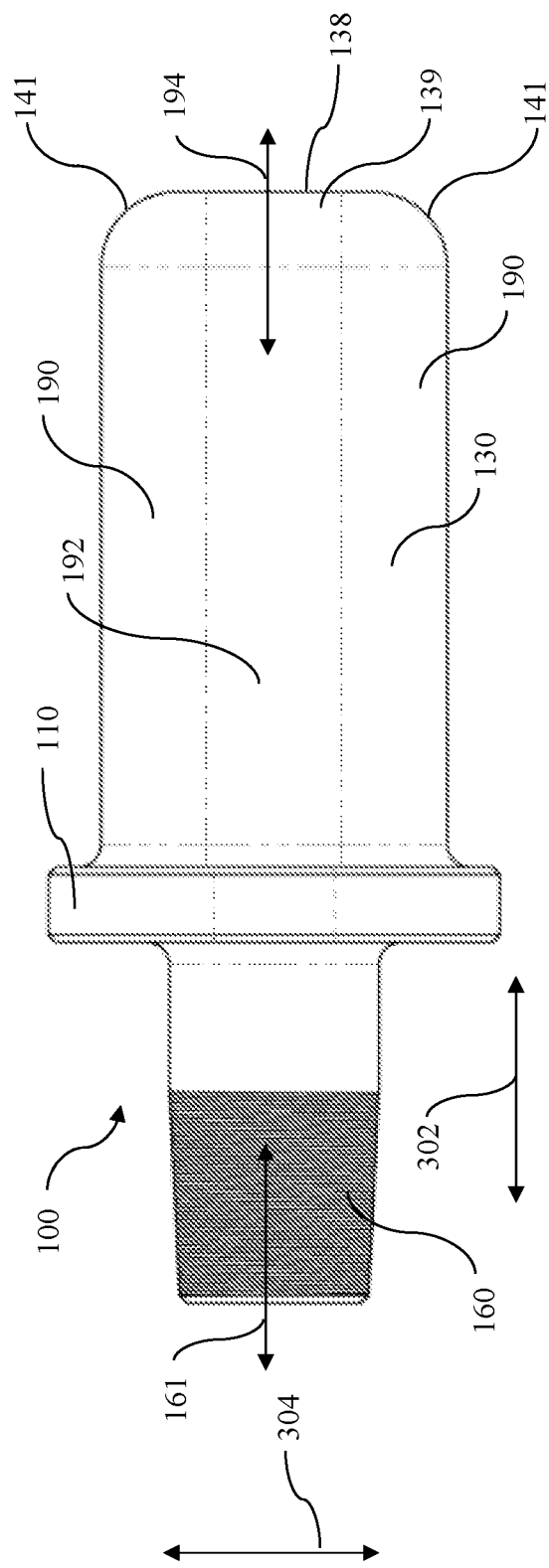

FEMORAL HEAD ARTHROPLASTY SYSTEM

CROSS-REFERENCE TO RELATED APPLICATION

This application is a divisional of U.S. patent application Ser. No. 16/899,230, filed Jun. 11, 2020, which claims priority to and the benefit of U.S. Provisional Patent Application No. 62/860,549, filed Jun. 12, 2019. The entirety of each of these applications is hereby incorporated by reference herein.

FIELD

The disclosed invention relates to hip implants, and, more particularly, to systems for securing a femoral head replacement to the femur of a subject.

BACKGROUND

Conventional hip implants are inserted into the femur about five to six inches. The use of such conventional hip implants requires removal of a significant quantity of a patient's bone, which can be undesirable. There is a need for hip implant systems that eliminate the need for removal of such significant quantities of bone.

SUMMARY

Described herein, in various aspects, is a femoral head arthroplasty system. The femoral head arthroplasty system can comprise a femoral prosthesis. The femoral prosthesis can comprise a mounting plate having a first side and an opposed second side, an adapter extending from the second side of the mounting plate, and an implant body extending from the first side of the mounting plate. The implant body can extend from the mounting plate by a distance no greater than 90 mm. A femoral head replacement can have a generally spherical surface and can comprise a recess that is shaped to complementarily receive the adapter of the femoral prosthesis.

A femoral head arthroplasty system can comprise a femoral prosthesis. The femoral prosthesis can comprise a mounting plate having a first side and an opposed second side, an adapter extending from the second side of the mounting plate, and an implant body extending from the first side of the mounting plate, wherein a distal end of the implant body has a planar face that is generally parallel to the mounting plate. A femoral head replacement can have a generally spherical surface and can comprise a recess that is shaped to complementarily receive the adapter of the femoral prosthesis.

A femoral head arthroplasty system can comprise a femoral prosthesis. The femoral prosthesis can comprise a mounting plate having a first side and an opposed second side. An implant body can extend from the first side of the mounting plate. The implant body can extend from the mounting plate by a distance no greater than 90 mm. The mounting plate and the implant body can cooperate to define a recess. A femoral head replacement can have a generally spherical portion and an adapter extending distally from the generally spherical portion. The adapter can be configured for complementary receipt within the recess of the femoral prosthesis.

The implant body can comprise at least one radially extending spline.

The implant body can comprise a plurality of radially extending splines.

The implant body can comprise a generally cylindrical portion.

The implant body can define a hemi-cylindrical surface.

The implant body can comprise mounting hardware. The mounting plate can define at least one opening configured to receive the mounting hardware.

The mounting hardware can comprise at least one screw.

The femoral prosthesis can comprise a porous or textured metal.

The porous or textured metal can be at least one metal selected from the group consisting of cobalt chromium, titanium, and tantalum.

The femoral prosthesis can comprise a coating.

The coating can be one selected from the group consisting of hydroxyapatite, titanium oxide, titanium nitride, zirconium oxide, and pyrolytic carbon.

The coating can be configured to promote ingrowth or on-growth of bone.

The diameter of at least a portion of the implant body can range from about 10 mm to about 18 mm.

The implant body can have a variable outer diameter.

The adapter can have a Morse taper.

The femoral head replacement can be angularly offset from the femoral prosthesis.

A method can comprise: forming a prepared site within a femur; and implanting a femoral head arthroplasty system such that the implant body is received within the prepared site, wherein the prepared site extends no more than 30 mm distal to the lesser trochanter of the femur.

The mounting plate can have a major dimension that is greater than or equal to a major radial dimension of the femur. The mounting plate can abut cortical bone at a cut proximal end of the femur.

A kit can comprise: a femoral prosthesis comprising: a mounting plate having an first side and an opposed second side, an adapter extending from the second side of the mounting plate, and an implant body extending from the first side of the mounting plate, wherein the implant body extends from the mounting plate by a distance no greater than 90 mm. The kit can further comprise a plurality of femoral head replacements, each femoral head replacement having a generally spherical surface and comprising a recess that is shaped to complementarily receive the adapter of the femoral prosthesis, wherein each femoral head replacement of the plurality of femoral head replacements differs from every other femoral head replacement of the plurality of femoral head replacements in size or material.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIG. 13 is a top view of the exemplary femoral prosthesis of FIG. 10.

FIG. 14 is a side view of the exemplary femoral prosthesis of FIG. 10.

Figure 1:
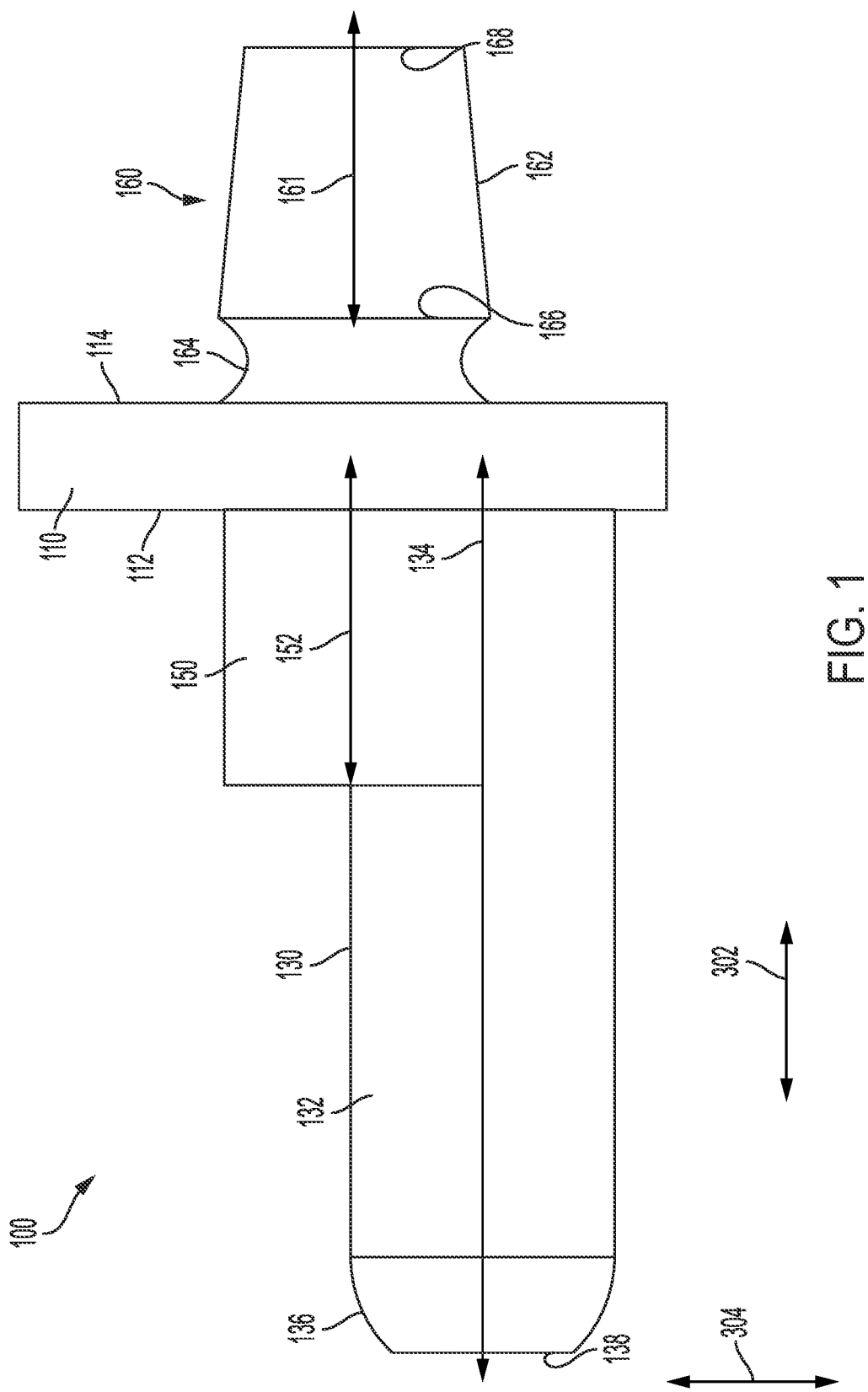
FIG. 1 is a side view of a femoral prosthesis of a femoral head arthroplasty system, in accordance with embodiments disclosed herein.
Figure 2:
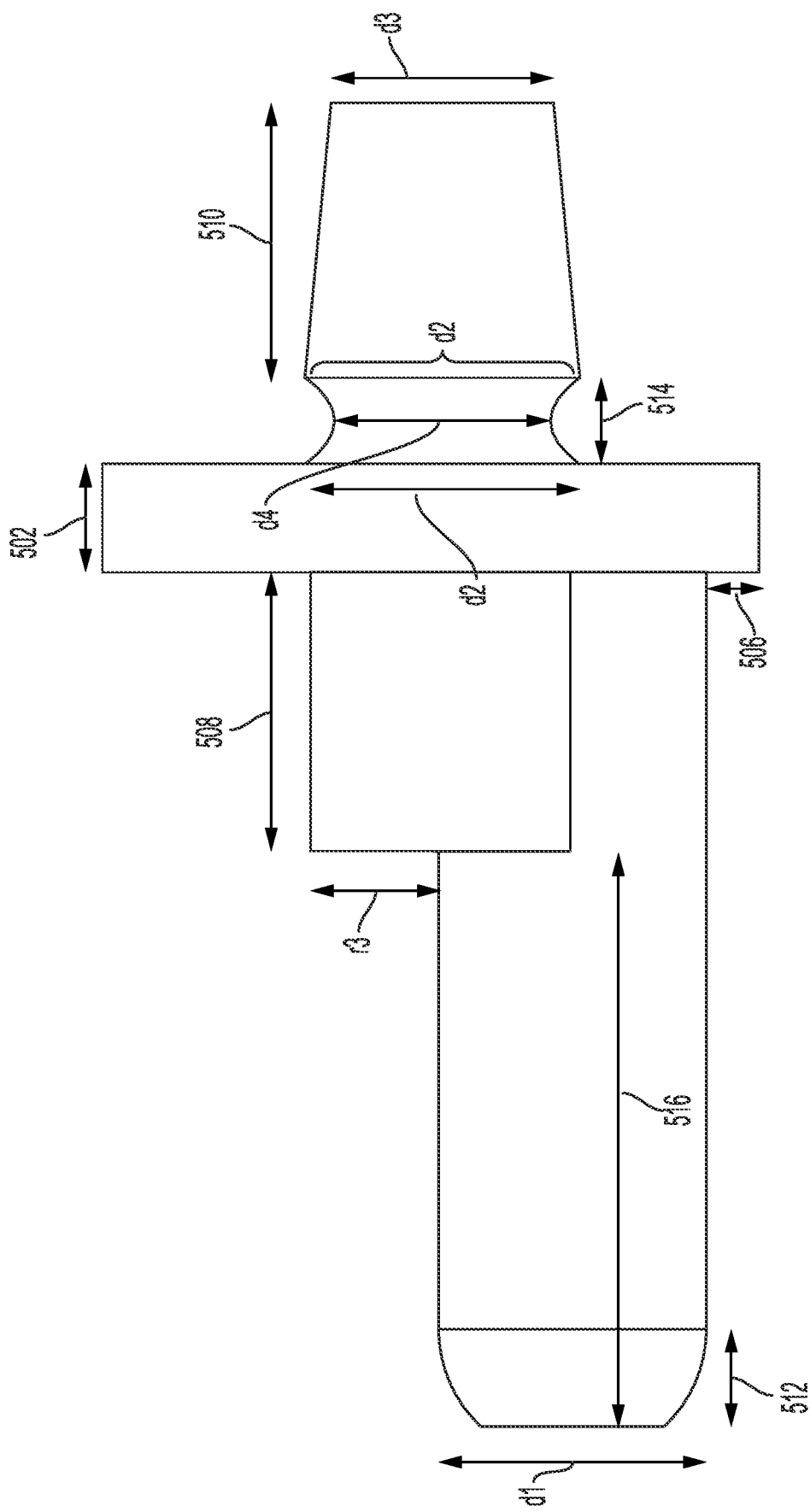
FIG. 2 is the side view of the femoral prosthesis of FIG. 1 with dimensions for one exemplary embodiment.
Figure 3:
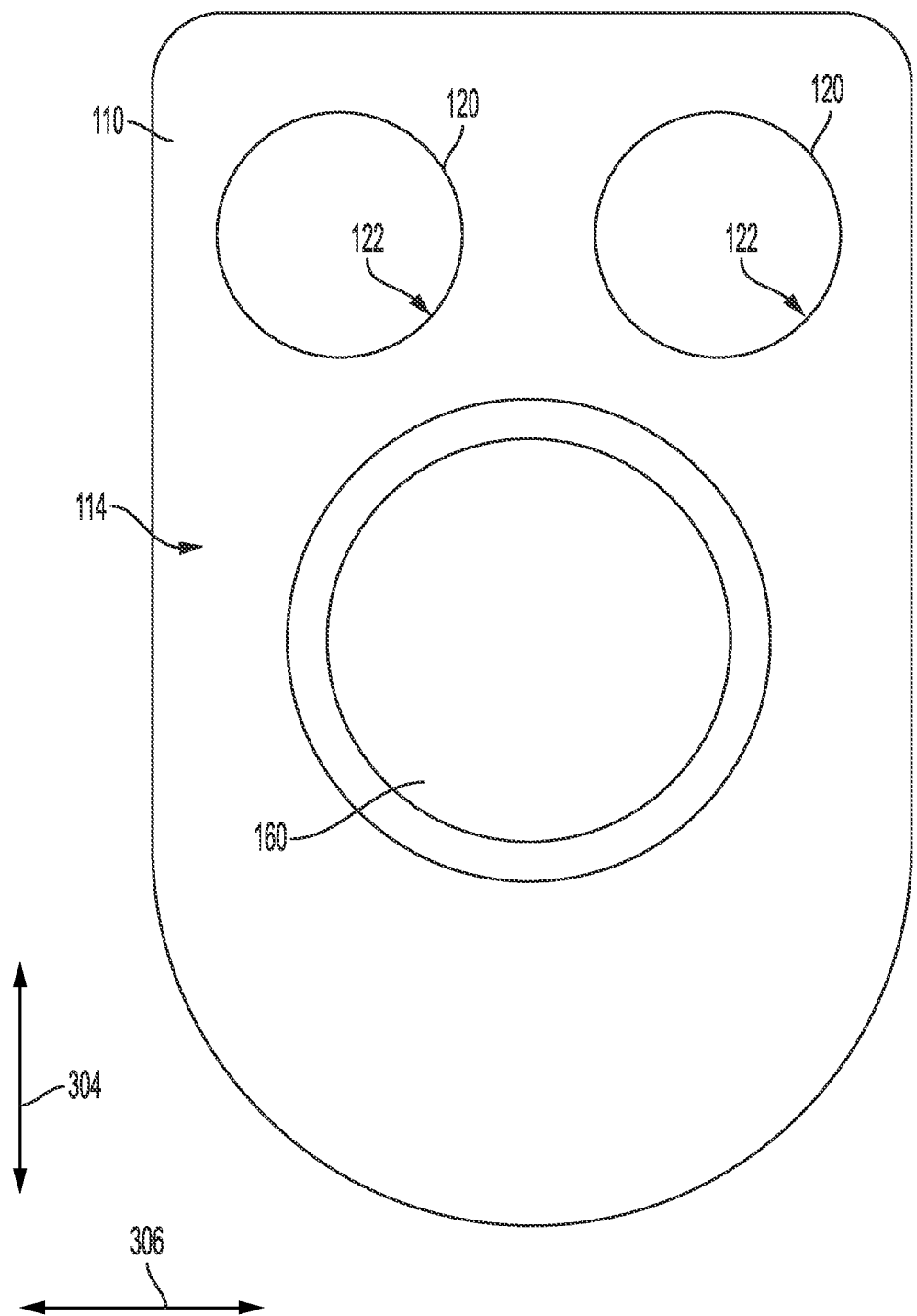
FIG. 3 is a front view of the femoral prosthesis of FIG. 1.
Figure 4:
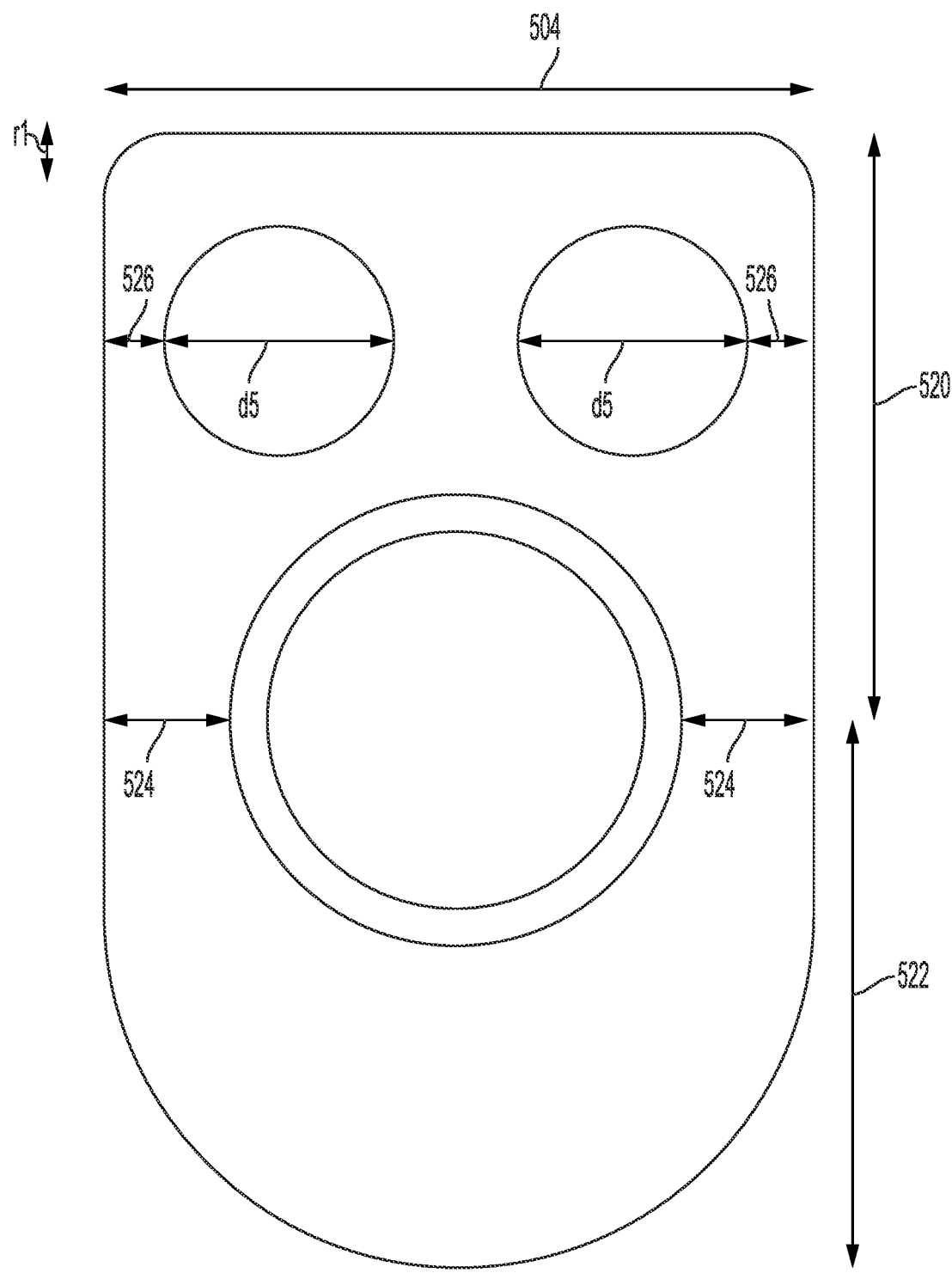
FIG. 4 is the front view of the femoral prosthesis of FIG. 3 with dimensions for one exemplary embodiment.
Figure 5:
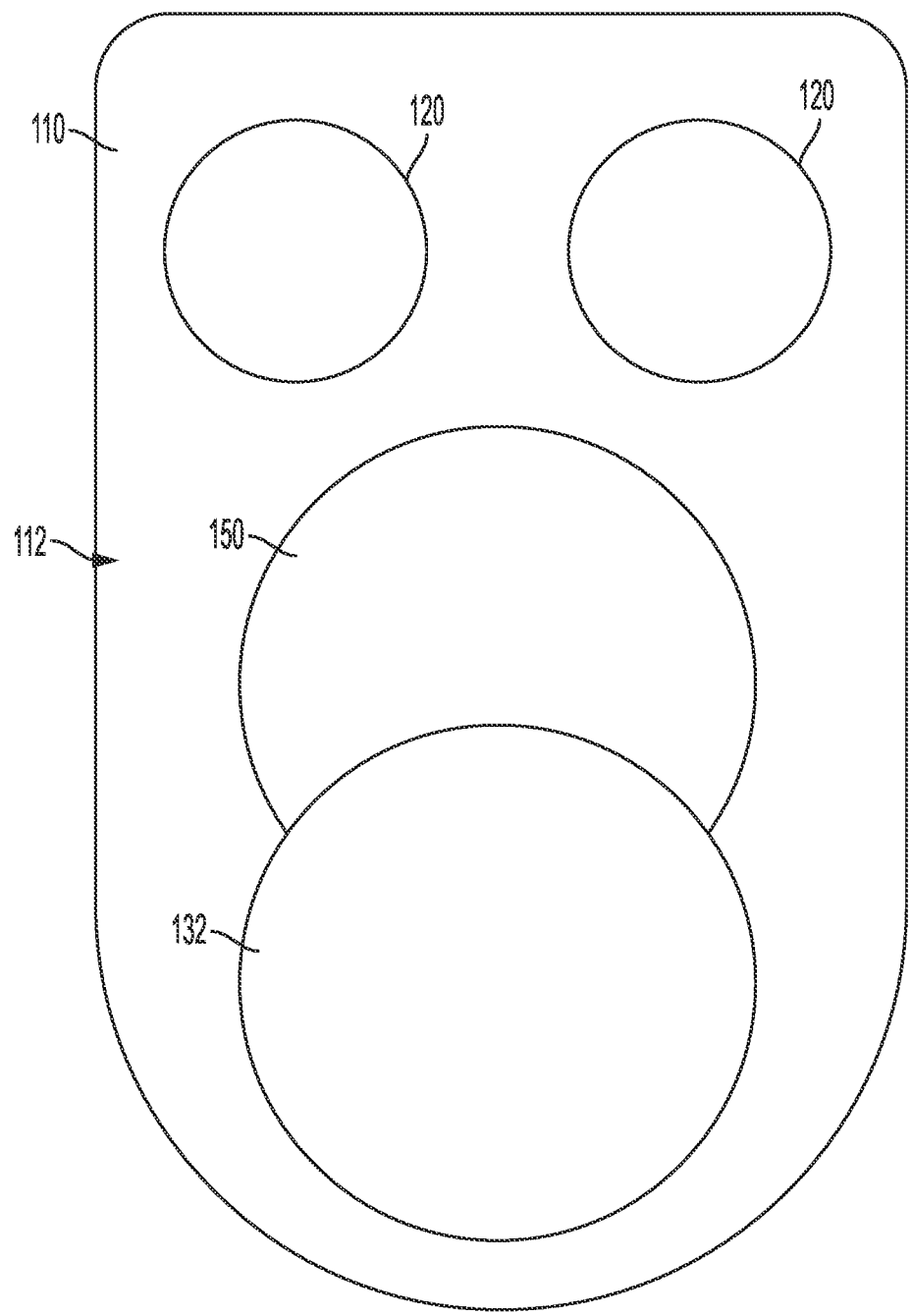
FIG. 5 is a rear view of the femoral prosthesis of FIG. 1.
Figure 6:
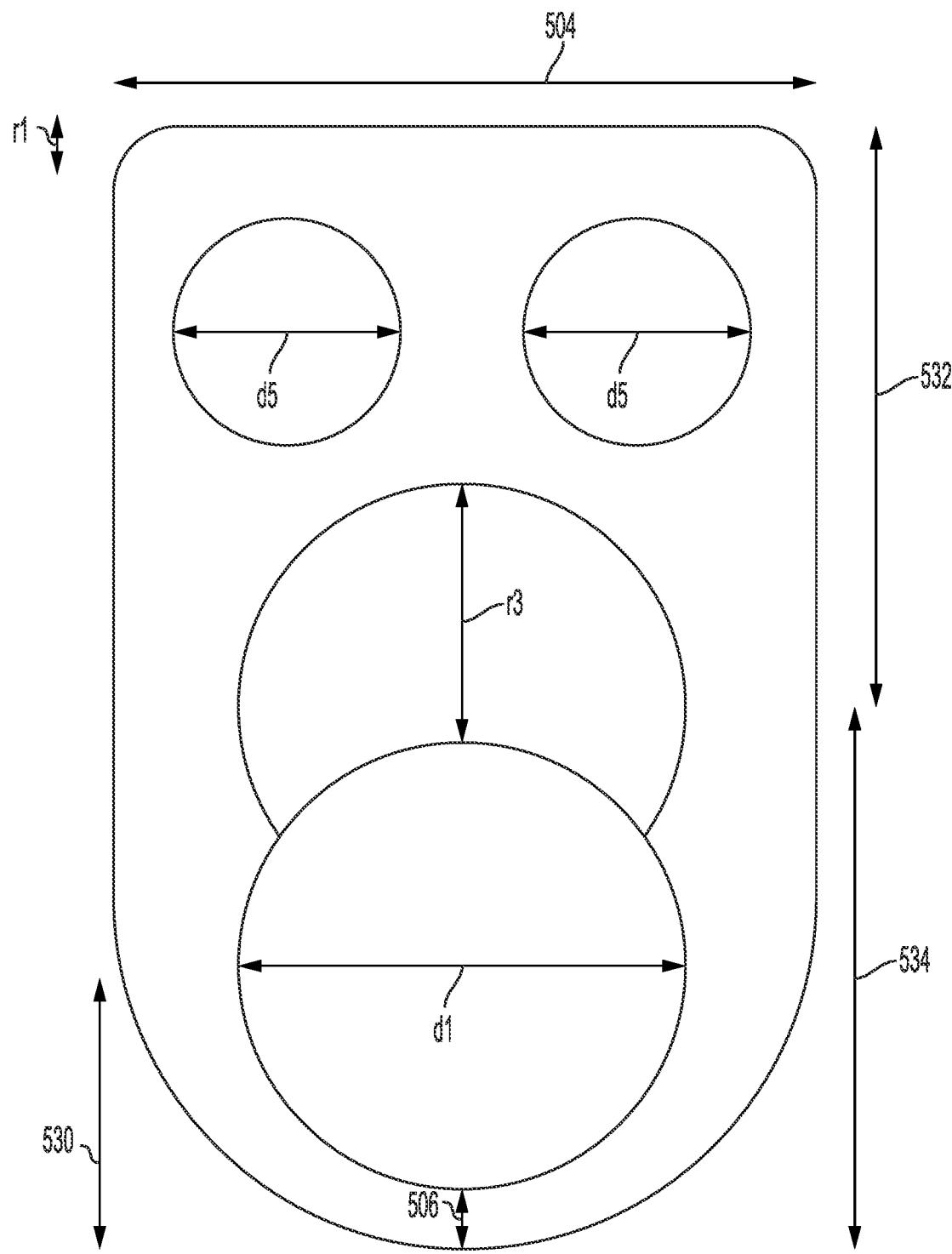
FIG. 6 is the rear view of the femoral prosthesis of FIG. 5 with dimensions for one exemplary embodiment.

It should be understood that any dimensions or other measurements indicated within the figures are merely exemplary and that other dimensions and measurements are contemplated.

DETAILED DESCRIPTION

The present invention now will be described more fully hereinafter with reference to the accompanying drawings, in which some, but not all embodiments of the invention, are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a screw" can refer to one or more of such screws, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, in some aspects, when values or characteristics are approximated by the use of the antecedent "approximately," "generally," or "substantially," it is contemplated that values within up to 15%, up to 10%, up to 5%, or up to 1% (above or below) of the particularly stated value or characteristic can be included within the scope of those aspects.

As used herein, the term "patient" can refer to a human or an animal that receives an implant as further disclosed herein. In exemplary aspects, a patient can be a human who has been determined to be in need of receiving an implant as disclosed herein.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Disclosed herein, in various aspects and with reference to FIG. 1, is a femoral prosthesis 100 of a femoral head arthroplasty system. The femoral prosthesis 100 can comprise a mounting plate 110 having a first side 112 and an opposing second side 114. The mounting plate 110 can have a planar or substantially planar profile and a thickness 502 between about three and about seven millimeters (e.g., about five millimeters) in a first dimension (measured along a first axis 302) that is perpendicular to the first side's surface. The mounting plate 110 can extend about twenty-five to about forty millimeters (e.g., about thirty-four millimeters) in a second dimension (measured along a second axis 304) and a length 504 of about sixteen to about twenty five millimeters (e.g., about twenty-two millimeters) in a third dimension (measured along a third axis 306). The femoral prosthesis's mounting plate 110 can have a major dimension that is greater than the major radial dimension of the patient's femur so that, when implanted within the femur, the mounting plate abuts the femur's outer radial wall. A pair of top corners can define a radius r1 (optionally, of about two millimeters), and a bottom of the mounting plate 110 can define a continuous arcuate profile (optionally, having a radius of eleven millimeters, or about half of the width of the mounting plate measured along the third axis 306).

The mounting plate 110 can define one or more through-holes 120 (e.g., a pair, as shown) that can receive mounting hardware for attaching the femoral prosthesis to a patient. The holes 122 can have respective diameters d5 (optionally, a diameter ranging from about 4 millimeters to about 10 millimeters, or more preferably, being about seven millimeters). In some aspects, the holes 122 can be spaced from respective side edges of the mounting plate by distances 526 (e.g., at least one millimeter, between one and 4 millimeters, or, more preferably, about two millimeters). The pair of through holes 120 can optionally define female threads 122 therein for receiving male threads of mounting screws (see also FIGS. 15 and 16). In some optional aspects, the pair of through holes 120 can be centered along the third axis 306 so that the femoral prosthesis is symmetrical about a plane that extends in the first and third dimensions (containing axes 302, 306) and bisects the femoral prosthesis 100. Although embodiments described herein comprise features for attachment via screws, in further embodiments, other attachment means, such as wires, sutures, or cables, may be used.

An implant body 130 can extend from the first side 112 of the mounting plate 110. The implant body 130 can be disposed below (i.e., offset in the second dimension (along second axis 304) from) the pair of through-holes 120. The implant body 130 can comprise a first cylindrical or generally cylindrical protrusion 132 that extends perpendicularly to the face of the mounting plate's first side 112. The first generally cylindrical protrusion 132 can extend less than ninety and greater than twenty millimeters, and optionally less than seventy-five and greater than thirty millimeters or between thirty-five and sixty millimeters, (e.g., about forty millimeters or about forty-five millimeters) from the first side 112 of the mounting plate along a first axis 134. The first generally cylindrical protrusion 132 can optionally have a diameter d1 between about ten and about eighteen millimeters (e.g., about fourteen millimeters). A distal end of the first generally cylindrical protrusion 132 (i.e., the end farthest away from the mounting plate 110) can have an arcuate edge 136 that extends a length 512 in the first dimension 302 ranging from about three millimeters to about eight millimeters, or more preferably, being about five millimeters. The distal end of the first generally cylindrical protrusion 132 can optionally have a planar face 138 that is generally parallel to the mounting plate. The first generally cylindrical protrusion 132 can be spaced from the bottom of the mounting plate 110, for example by about two millimeters. The first axis 134 of the first generally cylindrical protrusion 132 can optionally be spaced from the bottom of the mounting plate by a distance 530 (e.g., optionally, from about seven millimeters to about 12 millimeters, or about nine millimeters). In some optional aspects, the first generally cylindrical protrusion 132 can be spaced from the lower end of the mounting plate by a distance 506 (e.g., optionally, from about one millimeter to about four millimeters, or about two millimeters).

The implant body 130 can further comprise a second cylindrical or generally cylindrical protrusion 150 that extends along a second axis 152 that is parallel to the first axis 134. The second axis 152 can optionally be directly vertically above the first axis 134. The second generally cylindrical portion 150 can extend a length 508 about ten to about forty millimeters (e.g., from about ten millimeters to about twenty millimeters, or about fifteen millimeters) from the first side 112 of the mounting plate 110. The second generally cylindrical portion 150 can therefore have an end opposite the mounting plate 110 that is a length 516 (e.g., from about 25 millimeters to about 35 millimeters, or about thirty millimeters) from the end of the first generally cylindrical portion 130 opposite the mounting plate. The first and second axes 134, 152 can be spaced by less than the sum of the respective radiuses of the first and second generally cylindrical portions so that the second generally cylindrical protrusion 150 overlaps the first generally cylindrical protrusion 132. Accordingly, in a cross sectional plane perpendicular to the first axis 134, the overlapping first and second generally cylindrical protrusions 132, 150 can have a figure-eight shape. Optionally, the second axis 152 can extend along a top edge of the first generally cylindrical protrusion 132. The second axis 152 can be spaced from the top of the mounting plate by a distance 532 (e.g., optionally, from about 15 millimeters to about 20 millimeters, or about eighteen millimeters) and can be spaced from the bottom of the mounting plate by a distance 534 (e.g., optionally, from about 13 millimeters to about 18 millimeters, or about sixteen millimeters). That is, the second axis 152 can be spaced from the first axis by the radius of the first generally cylindrical protrusion 132. The second generally cylindrical protrusion 150 can have a radius r3 of about five to about nine millimeters (e.g., about seven millimeters). The first and second generally cylindrical protrusions 132, 150 can cooperate to provide an oblong cross section so that the implant body 130 is inhibited from rotation. Moreover, the combined cross sectional shape of the first and second generally cylindrical protrusions (e.g., a figure-eight shape) can cooperate with a bone preparation site that is easily prepared by a surgeon. In further embodiments, the implant body 130 can have various other cross sectional profiles in planes perpendicular to the implant body's longitudinal dimension, including a generally cylindrical profile, an oval profile, a polygonal profile (e.g., a square or rectangular profile), or an oblong profile.

Optionally, the implant body 130 can extend from the mounting plate by a distance of no greater than ninety millimeters, or no greater than seventy-five millimeters, or no greater than sixty millimeters, or no greater than fifty millimeters, or no greater than forty-five millimeters. As further disclosed herein, it is contemplated that the minimal length of the implant body 130 can reduce the amount of native bone of a subject that must be removed to accommodate the implant body.

An adapter 160 can extend from, and be oriented perpendicularly or substantially perpendicularly to, the second side 114 of the mounting plate 110. The adapter 160 can optionally have a central axis 161 that is collinear with the second axis 152. Accordingly, the adapter 160 can be superiorly axially offset from (i.e. above) the axis 134 of the first generally cylindrical protrusion 132. In this way, for some patients, a femoral head attached to the adapter 160 can most accurately recreate the patient's normal anatomy. In further embodiments, the adapter can have an axis offset from the axis 152. Optionally, in some such embodiments, the adapter 160 can be axially aligned with the axis 134. The adapter 160 can comprise a frustoconical portion 162 that attaches, via a neck portion 164, to the mounting plate 110. The neck portion can have a length 514 of from about three millimeters to about seven millimeters, or of about five millimeters. The frustoconical portion 162 can taper from a proximal end 166 to a distal end 168 (moving away from the mounting plate 110). The frustoconical portion 162 can optionally have a Morse taper. The proximal end 166 can optionally have a diameter d2 of about twelve to about sixteen millimeters (e.g., about fourteen millimeters), and the distal end 168 can optionally have a diameter d3 of about ten millimeters to about fourteen millimeters (e.g., about twelve millimeters). The frustoconical portion 162 can extend axially a length 510 of about ten to about eighteen millimeters (e.g., about fourteen millimeters) from the proximal end 166 to the distal end 168. In some aspects, the adapter's central axis can be spaced from the top of the mounting plate by a length 520 (optionally, from about 15 millimeters to about 20 millimeters, or about eighteen millimeters) and spaced from the bottom of the mounting plate by a length 522 (optionally, from about 13 millimeters to about 18 millimeters, or of sixteen millimeters). The adapter's radial-most surface can be spaced from the respective opposing side edges of the mounting plate in the third dimension 306 by a distance 524 (optionally, from about three millimeters to about six millimeters, or of about four millimeters). Optionally, at least a portion of the frustoconical portion's circumferential surface can comprise a texture. Said texture can improve frictional engagement between the adapter 160 and the femoral head replacement. In some optional aspects, a helical groove having a pitch of 0.5 millimeters can define said texture.

The neck portion 164 of the adapter 160 can have a cross section that varies along its axis in an arcuate profile. At a halfway point along its axis, the neck portion 164 can have a minimum diameter d4, which, in some embodiments, can be about twelve millimeters. Opposing ends of the neck portion 164 can each have a diameter d2 of about fourteen millimeters. Accordingly, the minimum diameter can be about two millimeters less than the maximum diameter of the neck portion 154. The neck portion's narrowing diameter can provide a location to grip the femoral prosthesis during implantation and removal of the femoral prosthesis.

Although shown extending parallel to the implant body 130, in further embodiments, the adapter 160 can extend at various angles with respect to the implant body 130 in order to vary the varus/valgus angle of the femoral head with respect to the longitudinal dimension of the femur.

Figure 7:
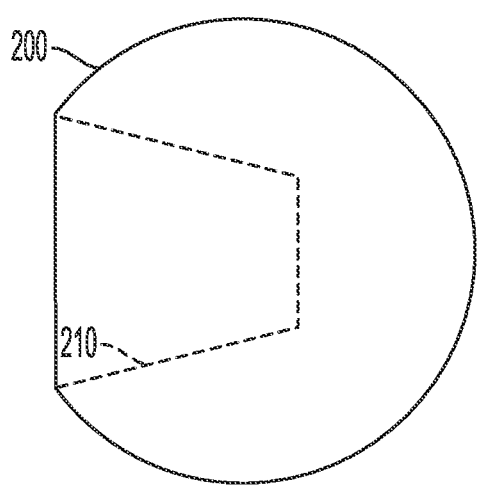
FIG. 7 is a side view of a femoral head replacement of the femoral head arthroplasty system for use with the femoral prosthesis of FIG. 1.

Referring to FIG. 7, the adapter 160 can receive a femoral head replacement 200. The femoral head replacement 200 can have a shape that cooperates with a hip socket of the patient's pelvis or an artificial hip socket. In some embodiments, the femoral head replacement 200 can have the shape of a natural femoral head. The femoral head replacement 200 can have a generally spherical profile. The femoral head replacement 200 can define a recess 210. The recess 210 can have a complementary shape to the adapter 160 (FIG. 1) of the femoral prosthesis 100 (FIG. 1). For example, the recess 210 can have a frustoconical profile. The prosthesis 200 can optionally be a conventional component known to those skilled in the art.

The femoral prosthesis 100 can couple to the femoral head replacement 200 to create a femoral head arthroplasty system 250. In some embodiments, the femoral prosthesis 100 and the femoral head replacement 200 can couple permanently, while in further embodiments, the pair can couple via a non-permanent means. The adapter 160 and femoral head replacement 200 can have an interference fit (e.g., via a Morse taper) so that the respective components frictionally engage each other. As stated above, at least one of the adapter 160 and the femoral head replacement 200 can optionally have a texture (i.e., surface texture) to improve the engagement between the respective components.

Figure 8:
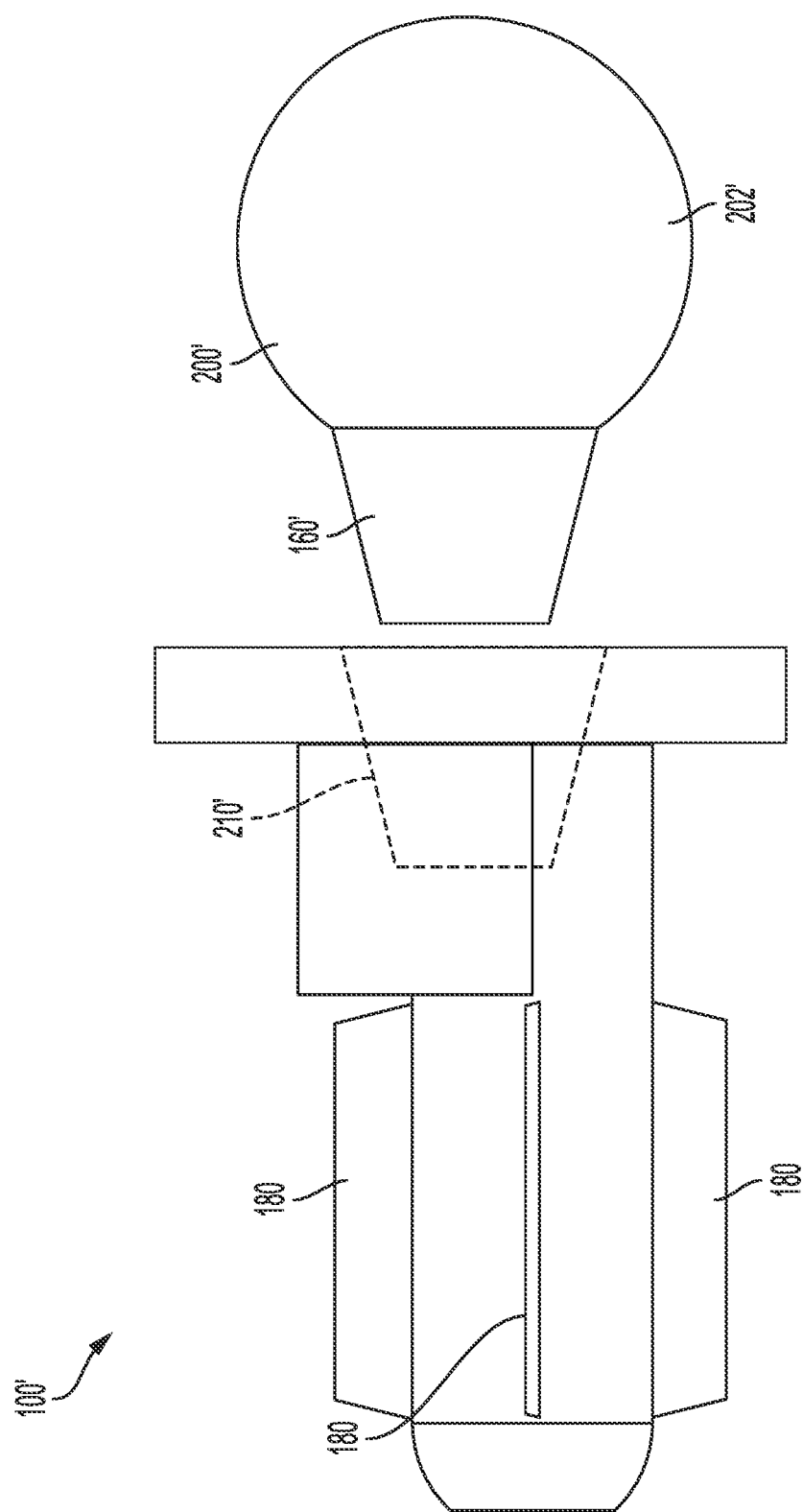
FIG. 8 is a side view of another embodiment of a femoral head arthroplasty system.

Referring to FIG. 8, in further embodiments, a femoral head replacement 200' can comprise a generally spherical portion 202' and an adapter 160' that extends distally from the generally spherical portion 202'. A femoral prosthesis 100' can comprise a recess 210' and can otherwise have the same shape and dimensions as that of the femoral prosthesis 100 (FIG. 1). Although shown as a frustoconical protrusion, the adapter 160' and recess 210' can have profiles similar to that of the adapter 160 (FIG. 1) and the recess 210 (FIG. 7), respectively, or any other adapter profile known to those skilled in the art.

In some embodiments, the femoral prosthesis can comprise at least one radially extending spline 180 or, as shown, a plurality of radially extending splines 180. The radially extending spline(s) 180 can provide surfaces against which bone can grow as well as inhibit rotation of the femoral prosthesis about its axis of elongation.

The femoral prosthesis 100 and/or the femoral head replacement 200 can comprise various materials known to those skilled in the art, such as, for example, porous, coated titanium, ceramics, tantalum, cobalt chromium alloy, or various other porous metals. The material(s) can be porous or textured in order to allow bone in-growth or on-growth. The material(s) can be strong enough to bear the weight of the patient without fracturing.

The femoral prosthesis 100 and/or the femoral head replacement 200 can comprise a coating. Said coating can comprise one or more of the following: hydroxyapatite, titanium oxide, titanium nitride, zirconium oxide, and pyrolytic carbon. In further embodiments, the coating can comprise gold, ceramics, polymers (e.g., ultra-high molecular weight polyethylene), diamond-like carbon (DLC) coatings, oxidized zirconium, titanium nitride or various other coatings known to those skilled in the art. The coating(s) can optionally be low friction and can optionally be hydrophobic.

Referring to FIGS. 10-14, in some aspects, the implant body 130 of the prosthesis 100 can have an elongate profile in the second dimension (along the second axis 304). That is, in cross sections perpendicular to the second axis 304, the implant body 130 can have a major dimension measured along the second axis 304 and a minor dimension measured along the third axis 306. For example, the implant body 130 can define two hemi-cylindrical surfaces 190 that are spaced along the second axis 304 and connected via planar faces 192. This or another non-axially symmetric profile can inhibit rotation of the implant body relative to the femur. In some aspects, the implant body can have a major dimension of between 18 and 25 millimeters (e.g., about 21 millimeters) measured along the second axis 304 and a minor dimension of between 12 and 18 (e.g., about 14 millimeters) measured along the third axis 306.

Figure 15:
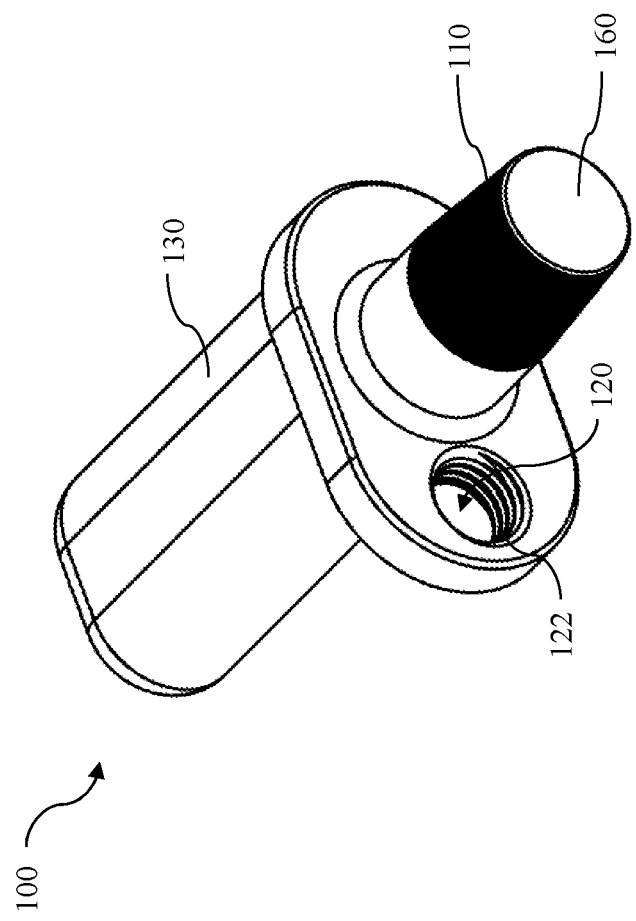
FIG. 15 is a perspective view of an exemplary femoral prosthesis in accordance with embodiments disclosed herein.
Figure 16:
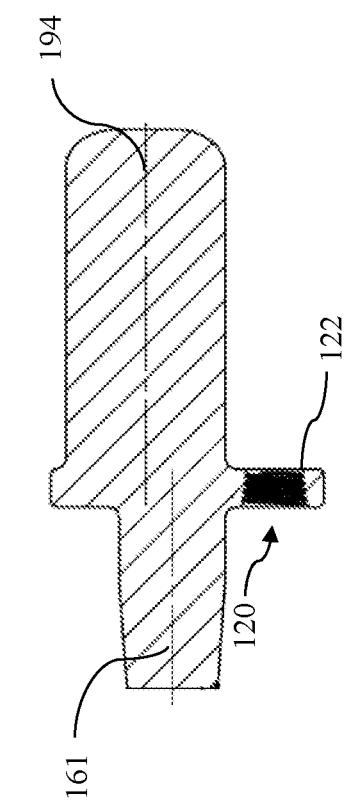
FIG. 16 is a cross sectional view of the exemplary femoral prosthesis of FIG. 15.
Figure 17:
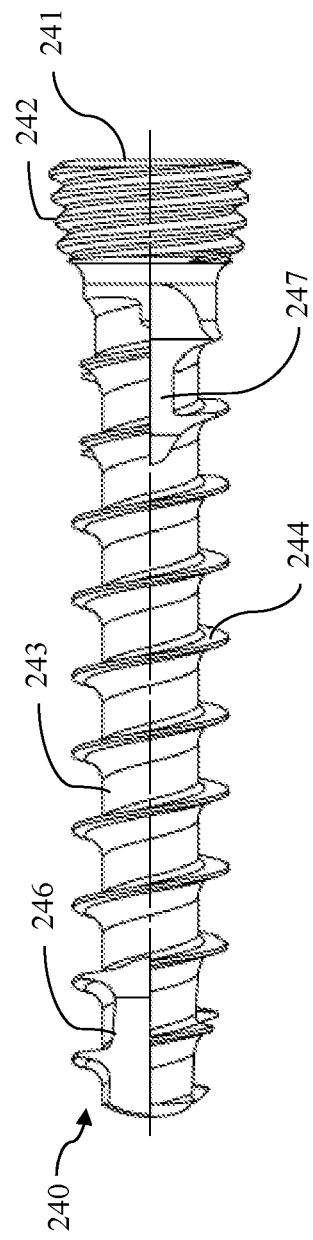
FIG. 17 is a side view of a fixation screw for use with the femoral prosthesis.
Figure 18:
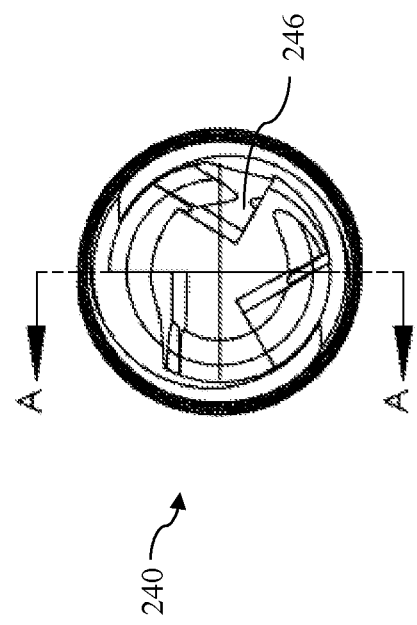
FIG. 18 is a first end view of the fixation screw of FIG. 17.
Figure 19:
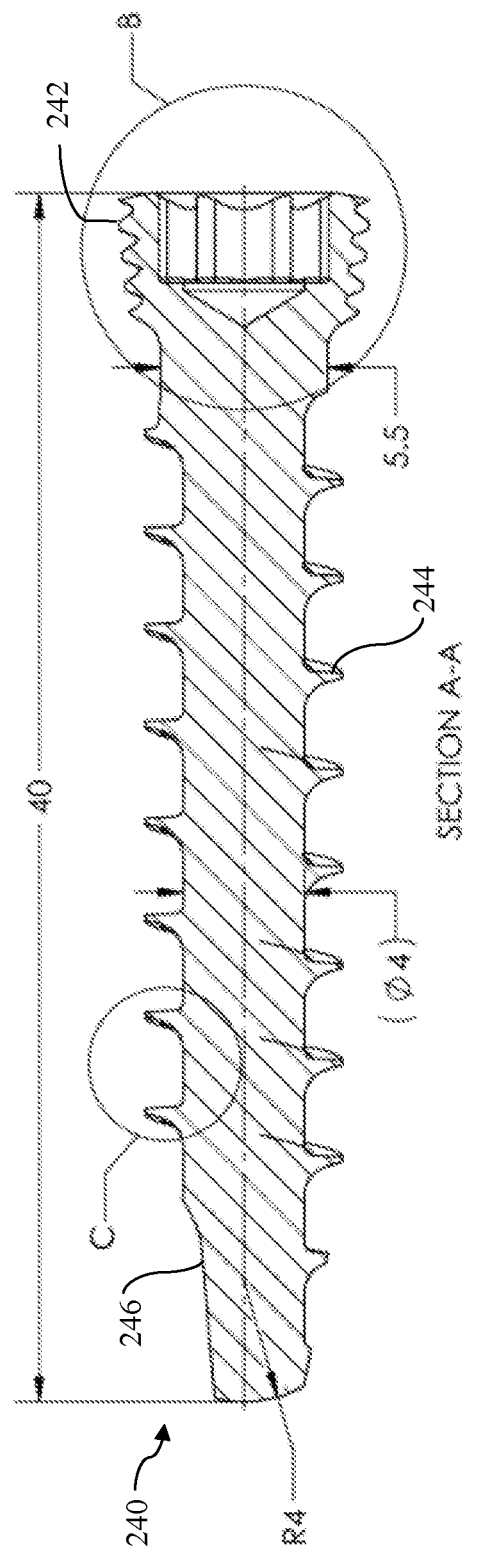
FIG. 19 is a cross sectional view of the screw taken in the plane A-A of FIG. 18.
Figure 20:
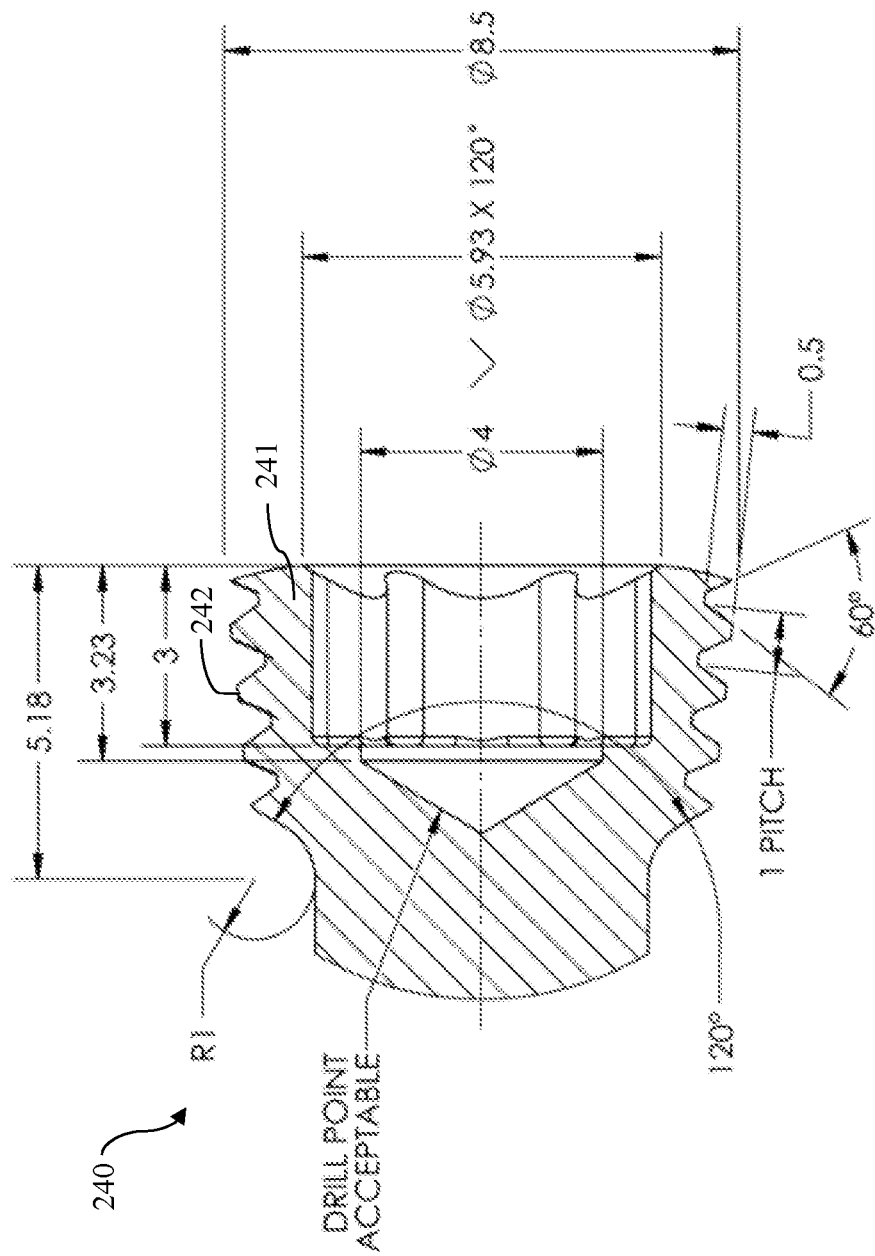
FIG. 20 is a detail view of the cross sectional view of the screw in FIG. 19 within the circle B.
Figure 22:
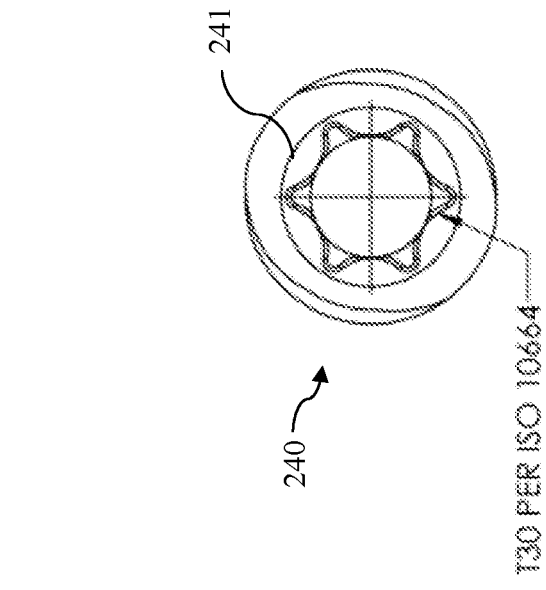
FIG. 22 is a second end view of the fixation screw of FIG. 17.
Figure 21:
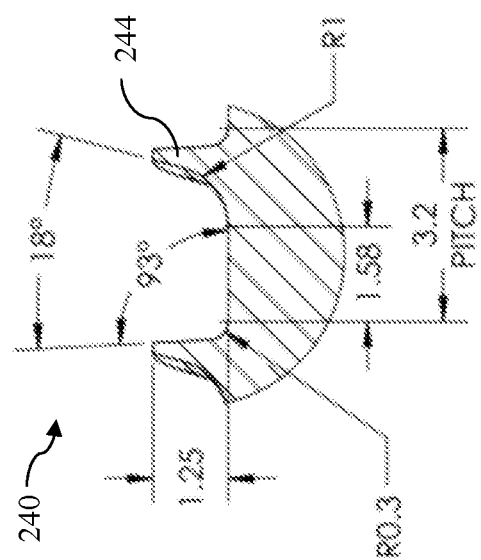
FIG. 21 is a detail view of the cross sectional view of the screw in FIG. 19 within the circle C.

In some optional aspects, the centerline 194 of the implant body (i.e., the line extending through the centroid of the cross sections in planes perpendicular to the first dimension (first axis 302)) can be collinear with the central axis 161 of the adapter 160. In further optional aspects, as shown in FIGS. 15 and 16, the centerline 194 can be offset from the central axis 161 of the adapter 160 (optionally, offset from the central axis 161 in the second dimension (relative to the second axis 304)).

In some optional aspects, the distal end of the implant body 130 can optionally have a planar face 138 that is parallel or generally parallel to the mounting plate. In further aspects, it is contemplated that the distal end of the implant body can define a rounded, oblong surface 139 or other non-planar surface that extends parallel to the mounting plate. For example, the implant body 130 can define first and second radii 141 (optionally, spherical surfaces) that are spaced relative to each other along the second dimension 304 (and that are measured in a plane containing the first and second axes).

In some aspects, the centerline 194 of the implant body can extend perpendicularly to the mounting plate 110 along an entire length of the implant body. For example, within any plane that intersects the implant body and is perpendicular to the first axis 302, a center point (which can optionally correspond to a center of mass) of the portion of the implant body within the plane will be intersected by the centerline 194. In further aspects, it is contemplated that the apparatus can be symmetric about a plane that is perpendicular to the second dimension 304 and bisects the implant body (and, therefore, includes the centerline 194). Optionally, in still further aspects, it is contemplated that the implant body can be symmetric about both (a) a first plane that is perpendicular to the second dimension 304 and bisects the implant body; and (b) a second plane that is perpendicular to the third dimension 306 and bisects the implant body. It is contemplated that the above-described configurations, by avoiding the need for providing an angled or asymmetric implant body (for example, as might be necessary to permit deeper advancement of an implant body within a native bone), can provide advantageous balance and force transmission properties while minimizing the amount of bone that is removed from the patient to accommodate the implant body.

Referring to FIGS. 10-14, it is further contemplated that in some aspects, the neck portion 164 can have a constant diameter (instead of the narrowing diameter as depicted in FIG. 1) to increase the strength of the prosthesis.

Referring to FIGS. 17-22, a fixation screw 240 can have a head 241 defining a first thread (or plurality of threads) 242 and a body 243 defining a second thread (or plurality of threads) 244. Optionally, the head of the screw can define a taper. Accordingly, the hole 120 (FIG. 16) can define a corresponding taper. The fixation screw can comprise one or more (e.g., optionally, three equally circumferentially spaced) self-tapping features 246 for tapping the bone during insertion of the screw. The fixation screw can further comprise one or more (e.g., optionally, three equally circumferentially spaced) self-tapping features 247 for tapping the bone during removal of the screw. It should be understood that the dimensions (in millimeters) provided in the figures should be understood to be optional aspects.

It is further contemplated that the prosthesis can be fixated to the femur, additionally or alternatively, with bone ingrowth and/or ongrowth and/or cemented fixation.

A kit can comprise a femoral prosthesis 100 and a plurality of femoral head replacements 200. Each of femoral head replacements 200 can differ from the others in at least one of size or material.

Figure 9:
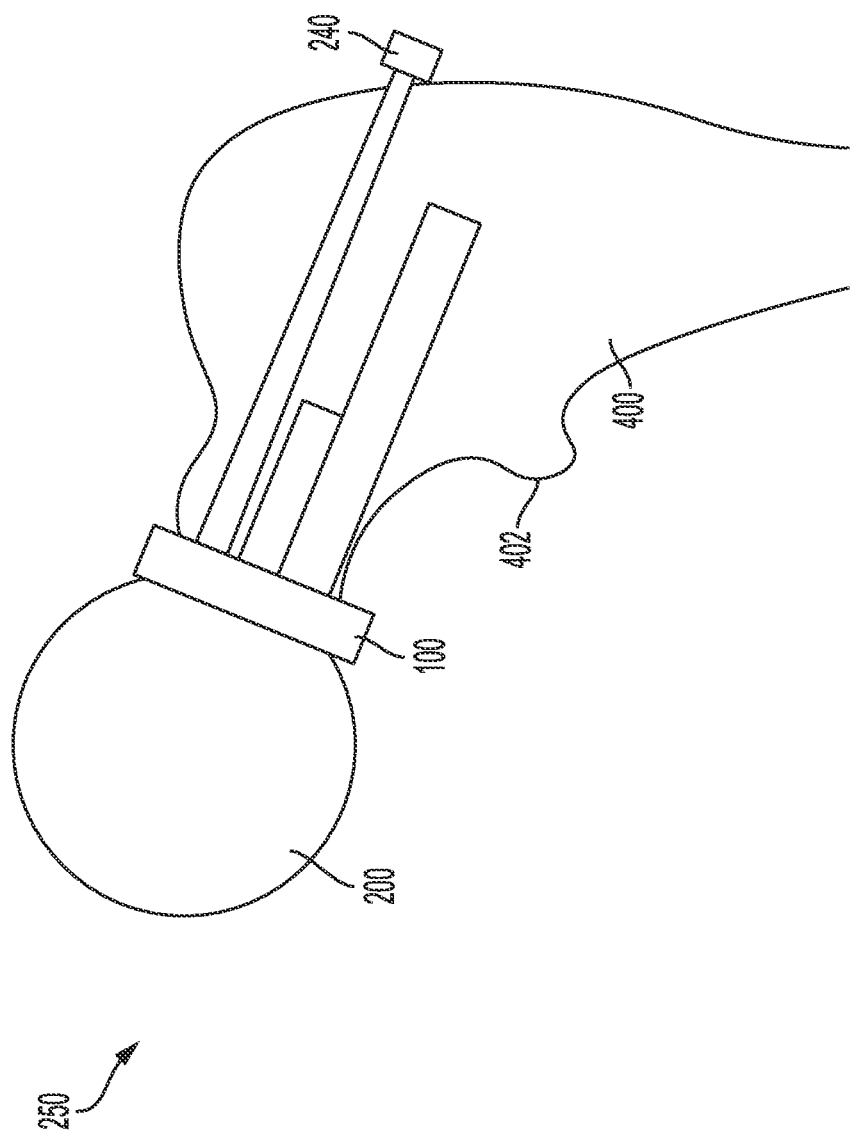
FIG. 9 is a partial cutaway view of a femoral head arthroplasty system installed in a femur.
Figure 10:
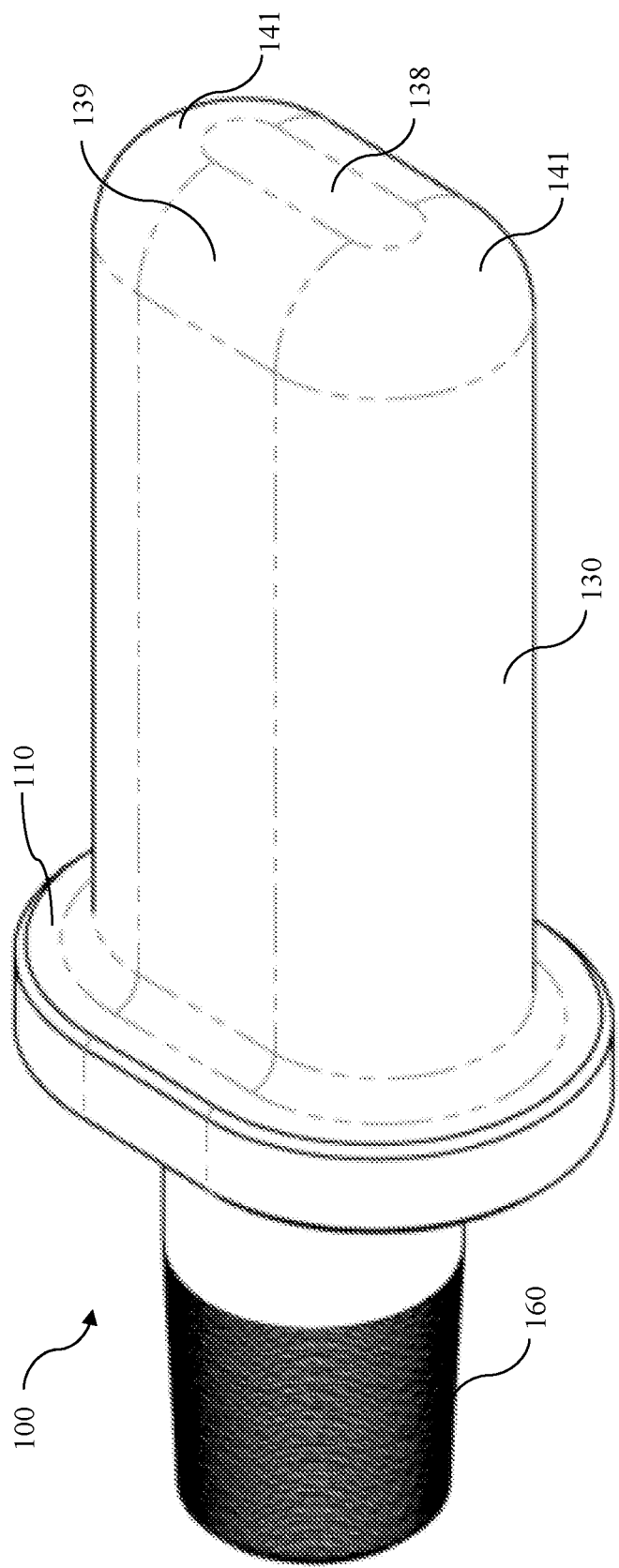
FIG. 10 is a rear perspective view of an exemplary femoral prosthesis in accordance with embodiments disclosed herein.
Figure 11:
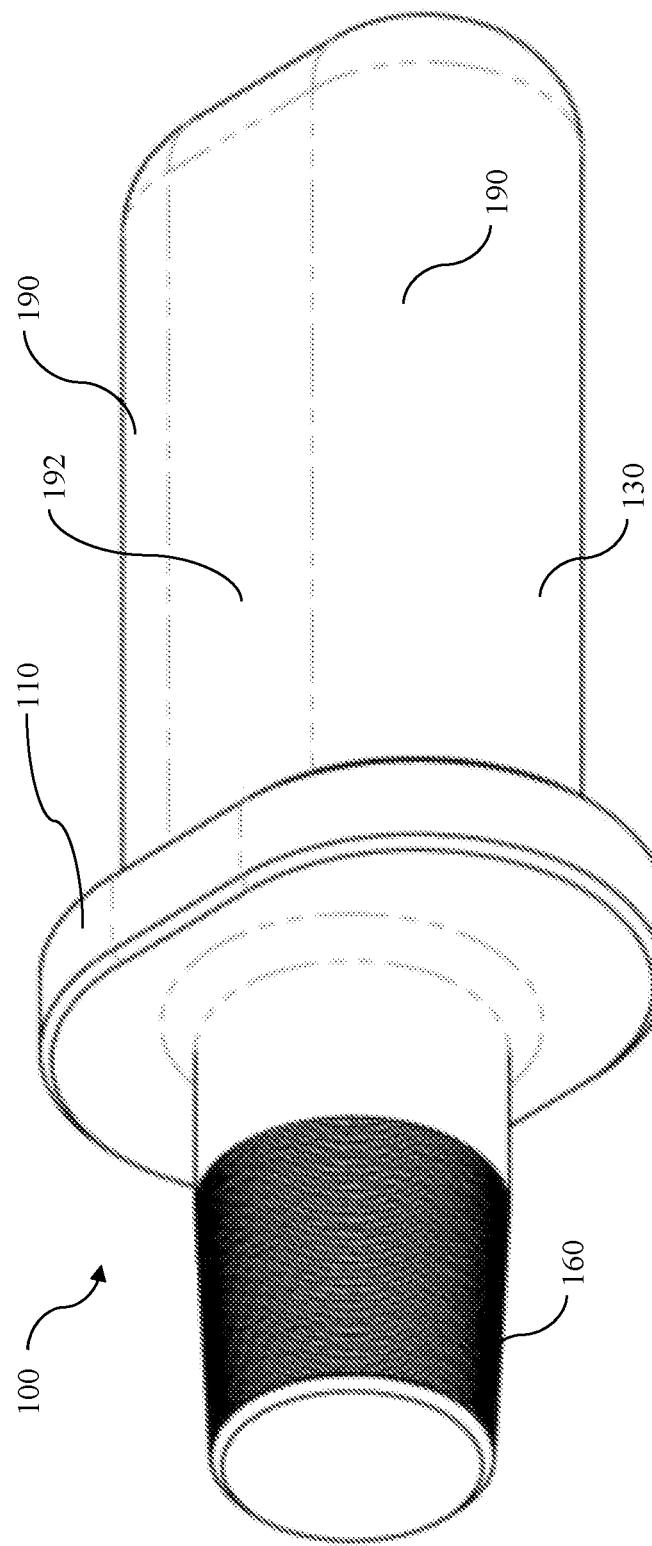
FIG. 11 is a front perspective view of the exemplary femoral prosthesis of FIG. 10.
Figure 12:
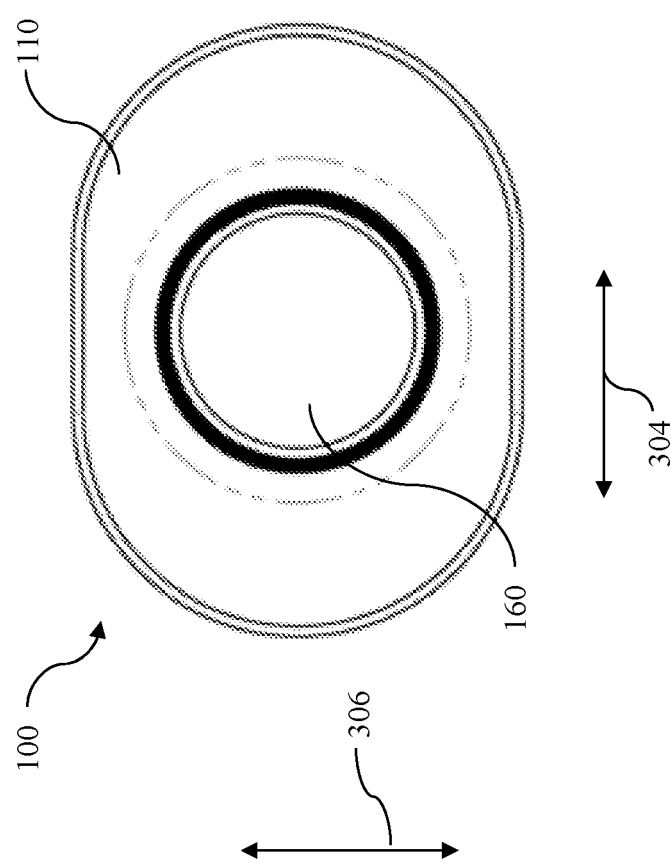
FIG. 12 is a front view of the exemplary femoral prosthesis of FIG. 10.

Referring to FIG. 9, a medical professional (e.g., an orthopedic surgeon) can form a prepared site within a femur 400. For example, the medical professional can cut off a portion of the patient's natural femoral head. Optionally, the surgeon can use a patient-specific cutting guide that locates the optimal location and angle for removing the femoral head. According to one embodiment, the cutting guide can comprise a frame that defines a slot for guiding a cutting saw. The cutting guide can temporarily be fastened to the femur using pins or screws and subsequently be removed from the femur after cutting. The surgeon can drill/ream a pair of overlapping holes to receive the first and second cylindrical portions 132, 150. In further aspects, the overlapping holes can further be bored to provide an opening to receive the implant body 130 (e.g., for the embodiments shown in FIGS. 10-14). The prepared site can be positioned further proximally along the neck of the femur (toward the original femoral head) than prepared sites of conventional femoral prostheses for hip replacement. The prepared site can optionally extend no more than thirty millimeters distal to the lesser trochanter 402 of the femur 400 (i.e., past the lesser trochanter along femoral shaft's longitudinal axis in the direction toward the patient's foot). The medical professional can then implant the femoral prosthesis so that the implant body is received within the prepared site. The femoral prosthesis can be inserted so that the mounting plate abuts a superior end of the femur. The medical professional can drill holes in the patient's bone for receiving the screws or other fasteners. Screws 240 or other fasteners can be used to secure the femoral prosthesis in place. When coupled to the mounting plate, the screws 240 or other fasteners can extend parallel to the implant body. Optionally, the surgeon can drill holes into the femur to receive screws 240. The femoral head replacement can then be attached to the femoral prosthesis.

Compared to conventional implants, embodiments disclosed herein can enable hip implants that require less bone removal. That is, a shorter segment of bone can be removed, leaving a portion of the femoral neck through which the femoral prosthesis can extend. The disclosed embodiments can reduce blood loss during surgery and enable easier insertion for the surgeon, particularly in cases of anterior approach surgery. The disclosed embodiments can be associated with smaller incisions than conventional implants and can provide for easier re-do surgery if need arises.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A femoral head arthroplasty system comprising: a femoral prosthesis comprising: a mounting plate having a first side and an opposed second side, an adapter extending from the second side of the mounting plate, and an implant body extending from the first side of the mounting plate, wherein the implant body extends from the mounting plate by a distance no greater than 90 mm; and a femoral head replacement having a generally spherical surface and comprising a recess that is shaped to complementarily receive the adapter of the femoral prosthesis.

Aspect 2: A femoral head arthroplasty system comprising: a femoral prosthesis comprising: a mounting plate having a first side and an opposed second side, an adapter extending from the second side of the mounting plate, an implant body extending from the first side of the mounting plate, wherein the implant body has a distal end, wherein the distal end of the body defines a surface that extends generally parallel to the mounting plate; and a femoral head replacement comprising a recess that is shaped to complementarily receive the adapter of the femoral prosthesis.

Aspect 3: A femoral head arthroplasty system comprising: a femoral prosthesis comprising: a mounting plate having a first side and an opposed second side; and an implant body extending from the first side of the mounting plate, wherein the implant body extends from the mounting plate by a distance no greater than 90 mm, wherein the mounting plate and the implant body cooperate to define a recess; and a femoral head replacement having a generally spherical portion and an adapter extending distally from the generally spherical portion, wherein the adapter is configured for complementary receipt within the recess of the femoral prosthesis.

Aspect 4: The femoral head arthroplasty system of aspects 1-3, wherein the implant body comprises at least one radially extending spline.

Aspect 5: The femoral head arthroplasty system of aspect 4, wherein the implant body comprises a plurality of radially extending splines.

Aspect 6: The femoral head arthroplasty system of any of aspect 1-3, wherein the implant body defines a generally hemicylindrical surface.

Aspect 7: The femoral head arthroplasty system of any of aspect 1-3, further comprising mounting hardware, and wherein the mounting plate defines at least one opening configured to receive the mounting hardware.

Aspect 8: The femoral head arthroplasty system of aspect 7, wherein the mounting hardware comprises at least one screw.

Aspect 9: The femoral head arthroplasty system of any of aspect 1-3, wherein the femoral prosthesis comprises a porous or textured metal.

Aspect 10: The femoral head arthroplasty system of aspect 9, wherein the porous or textured metal is at least one metal selected from the group consisting of cobalt chromium, titanium, and tantalum.

Aspect 11: The femoral head arthroplasty system of any of aspect 1-3, wherein the femoral prosthesis comprises a coating.

Aspect 12: The femoral head arthroplasty system of aspect 11, wherein the coating is one selected from the group consisting of hydroxyapatite, titanium oxide, titanium nitride, zirconium oxide, and pyrolytic carbon.

Aspect 13: The femoral head arthroplasty system of aspect 11, wherein the coating is configured to promote ingrowth or on-growth of bone.

Aspect 14: The femoral head arthroplasty system of any of aspect 1-3, wherein the diameter of at least a portion of the implant body ranges from about 10 mm to about 18 mm.

Aspect 15: The femoral head arthroplasty system of any of aspect 1-3, wherein the implant body has a variable outer diameter.

Aspect 16: The femoral head arthroplasty system of any of aspect 1-2, wherein the adapter has a Morse taper.

Aspect 17: The femoral head arthroplasty system of any of aspect 1-2, wherein the femoral head replacement is angularly offset from the femoral prosthesis.

Aspect 18: A method comprising: forming a prepared site within a femur; and implanting a femoral head arthroplasty system according to any one of aspect 1-17 such that the implant body is received within the prepared site, wherein the prepared site extends no more than 30 mm distal to the lesser trochanter of the femur.

Aspect 19: The method of aspect 18, wherein the mounting plate has a major dimension that is greater than or equal to a major radial dimension of the femur, and wherein the mounting plate abuts cortical bone at a cut proximal end of the femur.

Aspect 20: A kit comprising: a femoral prosthesis comprising: a mounting plate having a first side and an opposed second side, an adapter extending from the second side of the mounting plate, and an implant body extending from the first side of the mounting plate, wherein the implant body extends from the mounting plate by a distance no greater than 90 mm; and a plurality of femoral head replacements, each femoral head replacement having a generally spherical surface and comprising a recess that is shaped to complementarily receive the adapter of the femoral prosthesis, wherein each femoral head replacement of the plurality of femoral head replacements differs from every other femoral head replacement of the plurality of femoral head replacements in size or material.

Although the foregoing invention has been described in some detail by way of illustration and example for purposes of clarity of understanding, certain changes and modifications may be practiced within the scope of the appended claims.

What is claimed is:

1. A kit comprising: a femoral prosthesis comprising: a mounting plate having a first side and an opposed second side, wherein the first side of the mounting plate is configured to abut a cut proximal end of a neck of a femur, wherein the mounting plate defines a threaded opening that is configured to receive a first thread defined by a head of a screw; an adapter extending from the second side of the mounting plate; and an implant body extending perpendicularly from the first side of the mounting plate, wherein the implant body extends from the mounting plate by a distance no greater than 90 mm, wherein the implant body has a centerline that is perpendicular to the first side of the mounting plate, wherein the implant body is oblong in cross section in the plane that is perpendicular to the first axis, wherein the implant body has a distal end, wherein the implant body defines a continuous, uninterrupted circumferential surface extending from the mounting plate to the distal end, wherein the continuous, uninterrupted circumferential surface comprises two hemi-cylindrical surfaces having respective lengths, the two hemi-cylindrical surfaces being spaced along the second axis, and two parallel planar faces that are spaced along the third axis and extend between and to the two hemi-cylindrical surfaces along a respective entirety of each of the lengths of the two hemi-cylindrical surfaces; and a plurality of femoral head replacements, each femoral head replacement having a generally spherical surface and comprising a recess that is shaped to complementarily receive the adapter of the femoral prosthesis, wherein each femoral head replacement of the plurality of femoral head replacements differs from every other femoral head replacement of the plurality of femoral head replacements in size or material.

2. A femoral head arthroplasty system comprising: a femoral prosthesis comprising: a mounting plate having a first side and an opposed second side, wherein the first side of the mounting plate is configured to abut a cut proximal end of a neck of a femur, wherein the mounting plate defines a threaded opening that is configured to receive a first thread defined by a head of a screw; and an implant body extending from the first side of the mounting plate, wherein the implant body extends from the mounting plate by a distance no greater than 90 mm, wherein the implant body has a centerline that is perpendicular to the first side of the mounting plate, wherein the implant body is oblong in cross section in the plane that is perpendicular to the first axis, wherein the implant body has a distal end, wherein the implant body defines a continuous, uninterrupted circumferential surface extending from the mounting plate to the distal end, wherein the continuous, uninterrupted circumferential surface comprises two hemi-cylindrical surfaces having respective lengths, the two hemi-cylindrical surfaces being spaced along the second axis, and two parallel planar faces that are spaced along the third axis and extend between and to the two hemi-cylindrical surfaces along a respective entirety of each of the lengths of the two hemi-cylindrical surfaces; and a femoral head replacement having a generally spherical surface; wherein one of the femoral prosthesis and the femoral head comprises an adapter, and wherein the other of the femoral prosthesis and the femoral head defines a recess that is complementarily shaped to receive the adapter.

3. The femoral head arthroplasty system of claim 2, further comprising the screw having the head defining the first thread, wherein the screw comprises body defining a second thread.

4. The femoral head arthroplasty system of claim 3, wherein the mounting plate is configured so that when the head of the screw is received within the threaded opening, the screw extends parallel to the implant body.

5. The femoral head arthroplasty system of claim 2, wherein the femoral prosthesis comprises the adapter, wherein the adapter extends from the second side of the mounting plate.

6. The femoral head arthroplasty system of claim 2, wherein the femoral prosthesis comprises a porous or textured metal, wherein the porous or textured metal is at least one metal selected from the group consisting of cobalt chromium, titanium, and tantalum.

7. The femoral head arthroplasty system of claim 2, wherein the implant body comprises at least a portion of a cylindrical surface having a diameter from about 10 mm to about 18 mm.

8. The femoral head arthroplasty system of claim 2, wherein the implant body has a distal end portion having an arcuate surface spaced from the mounting plate along a longitudinal dimension, wherein the implant body has a consistent profile in planes perpendicular to the longitudinal dimension between the mounting plate and the distal end portion.

9. The femoral head arthroplasty system of claim 2, wherein the femoral head replacement is angularly offset from the femoral prosthesis.

10. The femoral head arthroplasty system of claim 2, wherein the implant body has a distal end, wherein the distal end of the body defines a surface that extends generally parallel to the mounting plate.

* * * * *